(12) United States Patent
Teicher et al.

(10) Patent No.: US 6,994,670 B2
(45) Date of Patent: Feb. 7, 2006

(54) METHODS FOR DIAGNOSING AKATHISIA

(75) Inventors: Martin H. Teicher, Waltham, MA (US); Elsa S. Palmer, Barrington, IL (US)

(73) Assignee: The McLean Hospital Corporation, Belmont, MA (US)

( * ) Notice: Subject to any disclaimer, the term of this patent is extended or adjusted under 35 U.S.C. 154(b) by 77 days.

(21) Appl. No.: 10/370,890

(22) Filed: Feb. 20, 2003

(65) Prior Publication Data

US 2004/0002636 A1 Jan. 1, 2004

Related U.S. Application Data

(60) Provisional application No. 60/358,882, filed on Feb. 22, 2002.

(51) Int. Cl.
 *A61B 5/00* (2006.01)

(52) U.S. Cl. ........................................ 600/300; 128/920
(58) Field of Classification Search ......... 600/300–301, 600/558–559, 595, 582; 128/904, 920, 898; 434/236–238, 322, 350
See application file for complete search history.

(56) References Cited

U.S. PATENT DOCUMENTS

| | | | |
|---|---|---|---|
| 5,011,413 A | 4/1991 | Ferris et al. | |
| 5,344,324 A | 9/1994 | O'Donnell et al. | |
| 5,801,810 A | 9/1998 | Roenker | |
| 5,940,801 A | 8/1999 | Brown | |
| 6,241,686 B1 | 6/2001 | Balkin et al. | |
| 6,280,198 B1 * | 8/2001 | Calhoun et al. | ............ 434/236 |
| 6,306,086 B1 | 10/2001 | Buschke | |

OTHER PUBLICATIONS

Gruber et al., "Wirkunen von Aktivierungsaufgaben bei akuter neuroleptikainduzierter" p. 30–37.*
Greenberg, "An objective measure of methylphenidale response: clinical use of the MCA," *Psychopharmacol. Bull*, 23(2):279–282 (1987).
Paulus et al., "The effects of MDMA and other methylene-dioxy–substituted phenylalkylamines on the structure of rat locomotor activity," *Neuropsychopharmacology* 7(1):15–31 (1992).
Rosvoid et al., "A continuous performance test of brain damage," *J. Consulting and Clinical Psychology* 20(5):343–350 (1956).
Teicher etal., "Objective measurement of hyperactivity and attentional problems in ADHD," *J. Am. Acad. Child Adolesc. Psychiatry* 35(3):334–342 (1996).

* cited by examiner

*Primary Examiner*—Max F. Hindenburg
*Assistant Examiner*—Michael C Astorino
(74) *Attorney, Agent, or Firm*—Clark & Elbing LLP; Paul Clark

(57) ABSTRACT

Provided are methods for diagnosing the presence, type, or severity of akathisia in a human subject. The methods involve using a computer-based system to assess impairment of certain cognitive and motor functions that are indicative of akathisia.

19 Claims, 1 Drawing Sheet

METHODS FOR DIAGNOSING AKATHISIA

CROSS REFERENCE TO RELATED APPLICATIONS

This application claims priority from U.S. Provisional Application Ser. No. 60/358,882, filed Feb. 22, 2002.

FIELD OF THE INVENTION

The invention relates to methods of diagnosing the presence, type, or severity of akathisia in a subject.

BACKGROUND OF THE INVENTION

Akathisia is one of the most serious and worrisome side effects of certain medications. Akathisia is characterized by physical restlessness, along with an inner state of mental restlessness or agitation that is disturbing and occasionally intolerable to the subject. Patients with akathisia often pace or move about excessively, and may feel restless, or that their muscles are itching, or that they are jumping out of their skin. Akathisia is associated with an increase in jerky foot tremors using tremorographic readings. Patients with akathisia have an intermittent low frequency (<4 Hz) tremor that occurs most frequently when patients are seated, and predominantly involves their lower extremities, though other body regions are affected in some individuals. Increased muscles tonus in one patient with acute akathisia has been reported.

Diagnosing akathisia can be very difficult because the diagnosis often hinges on clinical interview. For example, there are clinical rating scales, such as the Barnes Akathisia Scale, that may be used to evaluate akathisia. These rating scales provide only a subjective measure that depends on clinician skill and experience in observing and eliciting information from the subject. Many patients have difficulty providing some of the critical information. Some patients, such as children, or those who are psychotic and disorganized, are often unaware of and/or unable to describe medication side effects.

Actigraphs have been attached to subjects' ankles to record fluctuations in their level of ambulatory motor activity over a minimum of twenty-four continuous hours. Akathisia was associated with alterations in the pattern of circadian activity, although the activity measures were more strongly influenced by the nature of the patients' underlying psychiatric disorder that the degree of akathisia. Alterations in the pattern of circadian activity have been observed in schizophrenic patients with akathisia wearing actigraphs on their ankles. However, actigraphs worn on the ankle provide information about akathetic movement in the lower extremity only. While this is the most common site of akathetic movements, such movements may occur exclusively in other body parts, such as the head.

The medications that are known to produce akathisia as a side effect include antipsychotic or neuroleptic medications, some antidepressants, particularly the selective serotonin reuptake inhibitors, and the more noradrenergic tricyclic antidepressants, such as desipramine. Akathisia is the major reason for medication noncompliance, and has been linked to episodes of aggression, violence, and self-destructive behavior. However, given the difficulty in diagnosing akathisia, clinicians may attribute the deterioration in the patient's state to a worsening of his or her underlying psychiatric disorder. This misdiagnosis may lead to an increase in medication dose, which exacerbates rather than ameliorates the problem. Moreover, most attempts to diagnose akathisia focus exclusively on the physical aspect of akathisia.

There remains a need for methods of diagnosing the presence, type, or severity of akathisia in a subject. There is also a need for a method of diagnosing akathisia that can be preformed on the order of minutes, rather than hours.

SUMMARY OF THE INVENTION

The present invention provides a method of diagnosing the presence, type, or severity of akathisia in a human subject using computerized testing, which method includes the steps of: (a) placing, in proximity to said subject, a monitor that is connected to a computer, and a device that is controllable by the subject and that is also connected to the computer; (b) presenting to the subject instructions with respect to activating the device in response to visual images on the monitor; (c) presenting to the subject one or more of the visual images on the monitor; (d) storing in the computer the instances of device activation by the subject; and (e) scoring the accuracy or response time, or both, of device activation, wherein scoring below a pre-determined level is diagnostic for akathisia. Alternatively, more complex measures of subject response patterns may be analyzed.

In one embodiment of the invention, the method further includes the steps of: (f) using a motion analysis device connected to the computer to record the movements of the subject during presentation of the visual images; (g) storing the record of these movements in the computer; (h) analyzing the recorded movements for deviations from pre-determined norms; and (i) using the analysis of step (h) together with the scoring of step (e) in diagnosing dementia. The motion analysis device is preferably an infrared camera capable of detecting small infrared reflective markers. These markers can be placed at various positions on the subject, such as the head, elbow, and shoulders, in order to monitor the movements of these portions of the subject's body.

In one aspect, the invention takes advantage of the fact that akathisia is characterized by impaired vigilance in which there is a marked increase in the number of both commission errors and omission errors. In a preferred embodiment, the invention tracks movement of one or more body parts of a subject engaged in a monotonous task that elicits restlessness in an akathetic patient. In other preferred embodiments, the invention analyzes the spatial complexity of a subject's movement pattern to distinguish akathisia from hyperactivity. In another preferred embodiment, the invention provides simultaneous assessment of physical and mental restlessness or agitation by identifying disruption in capacity to remain focused on a monotonous but demanding vigilance task. The invention provides a more complete diagnostic picture than prior methods because it does not focus exclusively on the physical aspects of akathisia, but takes into account mental aspects as well.

Other features and advantages of the invention will be apparent from the following detailed description and from the claims.

BRIEF DESCRIPTION OF THE DRAWING

The FIGURE is a schematic diagram illustrating a computerized system that provides diagnostic information for assessing the presence or degree of akathisia.

DETAILED DESCRIPTION

Figure 1:
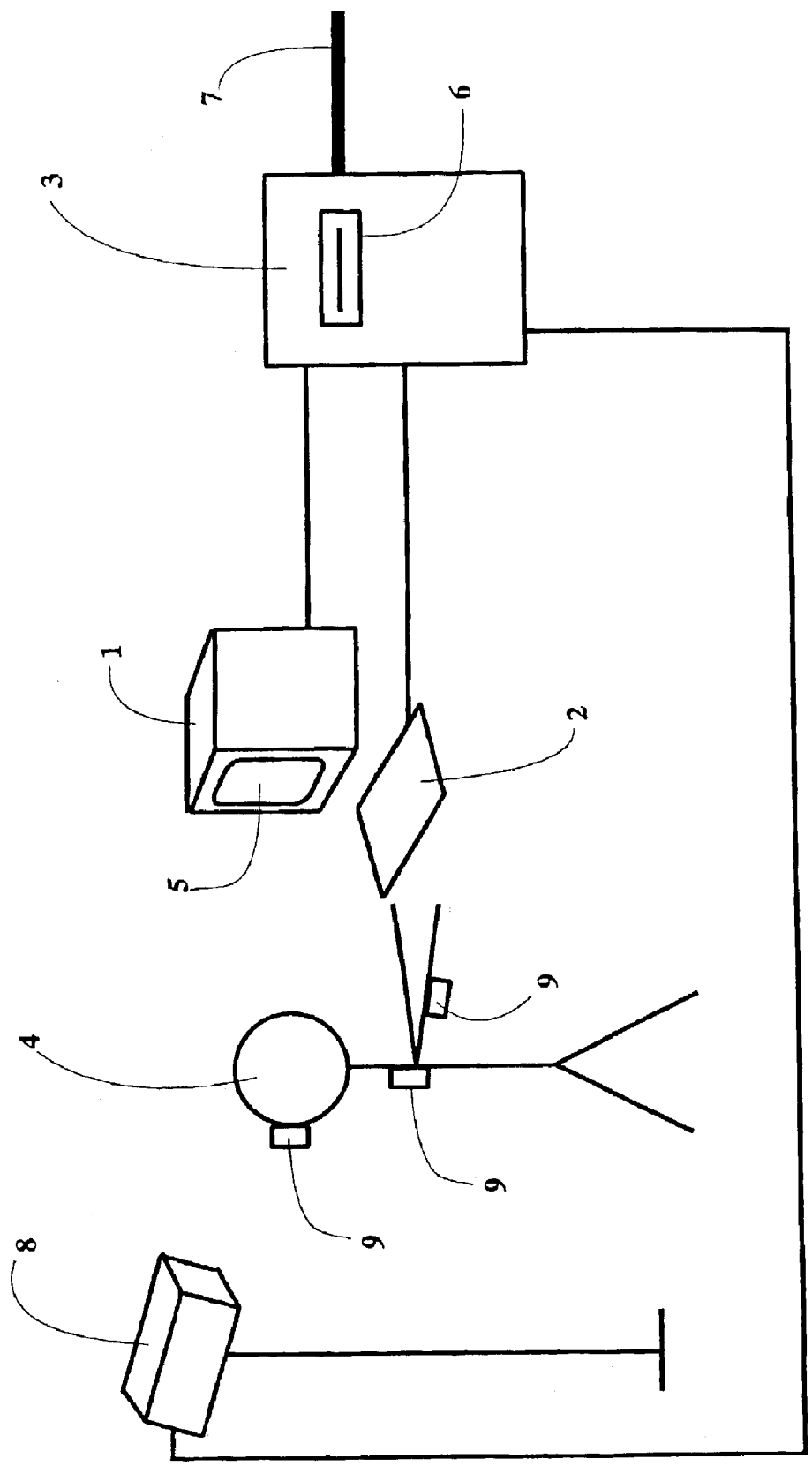

The present invention features a method for diagnosing the presence or severity of akathisia in a human subject. The method utilizes a computer-based system to assess impairment of certain cognitive and motor functions that are indicative of akathisia.

An embodiment of a system for performing a method of the invention is shown in the FIGURE. The system includes a monitor 1 that is a capable of displaying visual images on a screen 5. The monitor 1 is attached to a computer 3 and is positioned in proximity to a subject 4, so that the subject 4 may view the images displayed on the monitor screen 5. The computer 3 can be programmed to display a desired sequence of images, to which the subject 4 is instructed to respond by activating an input device 2 that is also attached to the computer 3 and is controllable by the subject 4. The input device 2 can be, for example, a standard computer keyboard, a hand-held plunger switch, or a large, easy-to-hit switch several (2–3) inches in length. When activated, the input device 2 sends the subject's inputs to the computer 3 which stores and analyzes the incidents of device activation.

The system may also include a motion analysis device 8 that is connected to the computer 3 and positioned so as to record the movements of the subject 4. Any video camera or other motion-sensing device capable of detecting the movements of the subject 4 can be used. For instance, the motion analysis device 8 can be an infrared motion analysis system (e.g., Qualisys, Glastonbury, Conn.) that includes a high-resolution CCD infrared video camera, an infrared strobe, and a video processor that provides hardware analysis of the video signal and outputs data to the computer 3. Such infrared motion analysis systems are known in the art, and are specifically designed to detect and record the precise vertical and horizontal position of small, light-weight infrared reflective markers 9. These markers 9 are attached to the subject 4 at various points, such as the head, shoulders, and elbows. As the subject 4 moves these portions of his or her body, the IR motion analysis system detects changes in the positions of the markers 9 and relays this information to the computer 3. Successive marker coordinates can be stored in the computer 3 and analyzed using commercially available software (e.g., OPTAX software, OptaxSystems, Inc., Burlington, Mass.).

The computer 3 can be a stand-alone personal computer, preferably with high computational capacity microprocessors. Alternatively, a minicomputer or mainframe computer can be used. The computer 3 can have a disc drive 6 into which the software that analyzes the subject's input's and/or movement patterns is loaded. In a preferred embodiment, the computer 3 has a connection 7 to a network of computers, such as a global computer network. This allows the computer 3 to exchange data with other computers connected to the network. In other preferred embodiments, the computer network is a local area network, a wide area network, an intranet, or an extranet. Thus, a subject may be tested not only in a clinical setting, but also at a remote location, such as the home, school, or workplace, thereby eliminating the inconvenience of traveling long distances for testing.

The system of the invention can be used to test certain cognitive and psychomotor functions that are diagnostic of akathisia. For instance, the capacity for sustained attention, control of impulses, reaction time, and regulation or inhibition of motor activity may be impaired in patients suffering from akathisia. Thus, by measuring these functions it is possible to distinguish normal patients from those with akathisia. The system can also be used to monitor these functions at different stages, in order to track the development and/or progression of akathisia.

The invention provides several advantages over previous methods of diagnosing akathisia. Some previous methods have focused exclusively on the physical aspect of akathisia. Vibrational measures, for example, are sensitive to movement in one plane of motion only, and provide no information about the spatial complexity of the movement pattern. The methods of the invention are highly sensitive to a disruption of in sustained attention and vigilance brought on by the mental distress of akathisia. In particular, the methods of the invention may be used to obtain precise information about movement in either the vertical or horizontal plane, or both, as well information about movement in the z-plane. Accordingly, unlike previous attempts, the invention has the capacity to distinguish akathisia from pseudoakathisia (excess movement without mental distress).

In addition, the invention provides several advantages over the use of actigraphs to diagnose akathisia. While actigraphic approaches require the subject to wear an ambulatory actigraph for a minimum of at twenty-four continuous hours, the present invention may detect the presence of akathisia in a matter of minutes. Moreover, actigraph measures are much more strongly influenced by the nature of the psychiatric disorder than the presence of akathisia, and thus lack the sensitivity and precision of the present invention. Furthermore, actigraphs worn on the ankle cannot provide information about akathetic movements in other body parts, where akathetic movements may occur exclusively.

Attention and Reaction Time

One way the system can be used to assess attention and reaction time is by providing the subject with a continuous performance task ("CPT") and recording the subject's performance. A typical CPT involves presenting the subject with a series of stimuli and instructing the subject to respond only to certain target stimuli. The subject's performance is scored based on the number of target stimuli correctly identified, the number of target stimuli missed, the number of responses to non-target stimuli, the number of non-target stimuli correctly missed, and the response time (e.g., U.S. Pat. No. 5,940,801).

For example, a subject's visual attention can be tested by displaying a series of visual stimuli on a computer screen, for which different responses are required of the subject. The stimuli can be any sort of visual image, including but not limited to, individual symbols, numbers, letters, or shapes, or a combination thereof. In one version of this test, the images are of two types and the subject is instructed to respond to only one type by activating the input device when the target stimuli appears on the screen. Typically, the test requires the subject to distinguish between two similar visual images, such as a five-pointed star and an eight-pointed star (see, e.g., Greenberg (1987), *Psychopharmacol. Bull.* 23:279–282 and Rosvold et al. (1956), *J. Consulting and Clinical Psychology* 20:343–350). For instance, the subject is instructed to press the space bar on the computer's keyboard if an eight-pointed star is displayed on the computer screen, and to do nothing when a five-pointed star appears on the screen. Data are collected for each individual image presented, including the type of stimulus (e.g., five-pointed star or eight-pointed star), whether or not the subject responded, and, if so, the amount of time the subject took to respond. From this raw data, the percentage of correct responses to the target stimulus, percentage of correct passes to the non-target stimulus, average response time, response time variability, and other statistics may be obtained. In addition, as is discussed below, a motion analysis device can be used to detect and record the subject's movement patterns throughout the test. At the end of the test, the recorded data (e.g., key press information and movement information) can be processed by the computer or transmitted over an Internet connection to a central processing station, where a report is generated and transmitted back to the testing site (e.g., U.S. Ser. No. 60/243,963).

Another CPT for assessing a subject's visual attention capabilities involves measuring the duration of time a particular visual stimulus must be present after a period of no stimulus before a subject can detect and respond to it (e.g., U.S. Pat. No. 5,801,810). For example, overall reaction time is estimated by presenting either a particular shape, such as a circle, or no stimulus (i.e., a blank screen) in random fashion. The subject is instructed to activate the input device as soon as possible after the circle appears on the screen, but not before. For both circle and no stimulus presentations, the percentage correct, the average response time, and variations about that average are stored, and provide a means for assessing deterioration in visual attention (See U.S. Ser. No. 60/204,663).

These CPTs may be used alone, together, or in conjunction with other well-known psychological tests for determining attention and reaction time. In one embodiment of the invention, the subject is asked to perform a series of CPTs starting with the circle/no stimulus CPT described above, followed by a CPT that requires the subject to distinguish between two different types of the same basic shape (e.g., five-pointed stars and eight-pointed stars). Testing of the subject's performance may be conducted with or without providing corrective feedback to the subject during performance of the CPT.

Motor Activity

Using the system of the invention, the movement abnormalities of a person with akathisia can be objectively discerned by measuring the frequency, amplitude, and pattern of body movements. As discussed above, very precise measurements of a subject's movements can be made using a motion analysis system that includes an infrared camera and one or more infrared reflective markers placed on the subject. These systems typically have a high spatial resolution (e.g. 40 $\mu$m) and can simultaneously track the vertical and horizontal movements of as many as 20 IR reflective markers. By using multiple IR cameras, it is possible to track the three-dimensional movements of the markers, if so desired.

Generally, the motor activity of the subject is monitored during performance of a CPT, such as those described above. Data is collected and sent to a computer to determine the time spent moving, number of movements, total distance and area traveled, and certain spatiotemporal measures of movement complexity. The computer, in addition to including the software required for running the CPT, contains software that performs the processing and analysis of the movement data (e.g. OPTAX Software).

Movement patterns of the subject can be analyzed using, for example, the procedures described in Paulus, M., Geyer, M. (1992), *Neuropsychopharmacology* 7:15–31 and Teicher et al. (March 1996), *J. Am. Acad. Child Adolsec. Psychiatry* 35(3): 334–342, which are based on the concept of microevents. A new microevent begins whenever the marker moves more than a predetermined distance (e.g., 1.0 mm or more) from the location of the previous microevent, and is defined by its position and duration. From the sequence of microevents, the mean locomotor path length can be calculated, along with two scaling exponents. The first exponent, the spatial scaling exponent, is a measure of the complexity of the movement and is calculated by ascertaining the logarithmic rate of information decay at progressively lower levels of resolution. Conceptually, if a marker is still or moving in a straight line, no information is lost if the marker's position is sampled less frequently. The total distance traversed can still be calculated. On the other hand, if a marker is moving in a convoluted path, then less frequent sampling smooths out the route and underestimates the distance traveled. Spatial complexity corresponds to the concept of fractal dimensions and ranges from 1.0 (straight line movement) to 2.0 (complex, convoluted movement patterns).

The other exponent, known as the temporal scaling exponent, is calculated from the log-log relationship between the frequency of the microevents and their duration. For a two-process model in which a marker is either in motion or immobile, stochastic theory dictates that there will be a greater number of brief periods of immobility than long periods of immobility (though not necessarily a greater amount of time). The log-log relationship provides a robust measure of relative activity versus inactivity and indicates the degree to which a subject is moving in the environment.

Since humans suffering from akathisia exhibit abnormal motor activity and impaired cognitive functioning, the data collected concerning a subject's movement patterns and CPT performance can be compared to those of akathetic and non-akathetic patients to determine whether the subject has akathisia. If so, the data can be used to ascertain not only the severity of the akathisia, but also its etiology, thereby allowing the attending physician to determine the most appropriate course of treatment.

In one embodiment, the invention may be used to assess a subject's level of physical and mental agitation prior to initiation of treatment with a medication or drug that could produce akathisia as a side effect, e.g., antipsychotic or neuroleptic medications, some antidepressants, particularly the selective serotonin reuptake inhibitors, and the more noradrenergic tricyclic antidepressants, such as desipramine. The subject may then be reassessed after administration of the drug. For example, the subject may be reassessed at after a predefined time period based on what is known about the time course for development of akathisia for the particular medication. If akathisia is detected, the clinician may modify the subject's therapeutic regimen, and reassess the subject to determine whether the modifications successfully ameliorated the akathisia.

Other Embodiments

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein.

All publications, patents, and patent applications mentioned in this specification are hereby incorporated by reference.

What is claimed is:

1. A method of diagnosing akathisia in a subject comprising the steps of:
   (a) placing, in proximity to said subject, (i) a monitor that is connected to a computer, and (ii) a device that is controllable by said subject and that is also connected to said computer;
   (b) presenting to said subject instructions with respect to activating said device in response to visual images on said monitor;
   (c) presenting to said subject one or more of said visual images on said monitor;
   (d) storing in said computer the instances of device activation by said subject; and
   (e) scoring the accuracy or response time, or both, of device activation, wherein scoring below a level characteristic of non-akathetic patients is diagnostic for akathisia.

2. The method of claim 1, further comprising the steps of:

(f) using a motion analysis device connected to said computer to record movements of said subject during presentation of said visual images;

(g) storing the record of said movements in said computer;

(h) analyzing said recorded movements for deviations from pre-determined norms; and (i) using the analysis of step (h) together with the scoring of step (e) in diagnosing akathisia.

3. The method of claim 2, wherein said motion analysis device is a video camera.

4. The method of claim 3, wherein said camera is an infrared camera capable of detecting an infrared reflective marker.

5. The method of claim 4, wherein at least one infrared reflective marker is placed onto said subject.

6. The method of claim 5, wherein said marker is positioned on the head of said subject.

7. The method of claim 5, wherein at least three markers are placed onto said subject.

8. The method of claim 7, wherein said markers are positioned on the head, elbow, and shoulders of said subject.

9. The method of claim 1, wherein said pre-determined level is determined prior to the administration of a substance to the subject.

10. The method of claim 9, wherein the substance is a drug.

11. The method of claim 10, wherein the drug is selected from an antipsychotic medication, a neuroleptic medication, an antidepressants, and a selective serotonin reuptake inhibitor.

12. The method of claim 1, wherein said computer is connected to a second computer via a network and said instructions or said images are conveyed to said subject across the network.

13. The method of claim 12, wherein the network is selected from a global computer network, a local area network, a wide area network, an intranet, and an extranet.

14. The method of claim 2, wherein said movements are recorded while said subject is performing a continuous performance task.

15. The method of claim 1, wherein said visual images are selected from the group consisting of symbols, numbers, letters, and shapes.

16. The method of claim 15, wherein said subject is instructed to activate said device when a specified image is displayed on said monitor.

17. The method of claim 15, wherein said visual images comprise stars.

18. The method of claim 17, wherein said visual images comprise five-pointed stars and eight-pointed stars.

19. The method of claim 17, wherein said subject is instructed to activate said device when a star having a specified number of points is displayed on said monitor.

* * * * *

UNITED STATES PATENT AND TRADEMARK OFFICE
CERTIFICATE OF CORRECTION

| | | |
|---|---|---|
| PATENT NO. | : 6,994,670 B2 | Page 1 of 1 |
| APPLICATION NO. | : 10/370890 | |
| DATED | : February 7, 2006 | |
| INVENTOR(S) | : Teicher et al. | |

It is certified that error appears in the above-identified patent and that said Letters Patent is hereby corrected as shown below:

On the Title Page, in References Cited, in OTHER PUBLICATIONS, in Teicher et al., replace "Teicher etal.," with --Teicher et al.,--.

Column 1, Line 45, replace "that" with --than--.

Column 4,
    Line 3, replace "in sustained attention" with --sustained attention--; and
    Line 14, replace "at twenty-four" with --at least twenty-four--.

Column 8, Claim 11, Line 3, replace "antidepressants" with --antidepressant--.

Signed and Sealed this

Fifteenth Day of May, 2007

JON W. DUDAS
*Director of the United States Patent and Trademark Office*